(12) United States Patent
Maschke

(10) Patent No.: US 7,643,885 B2
(45) Date of Patent: Jan. 5, 2010

(54) INTRAVENOUS PACEMAKER ELECTRODE

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 642 days.

(21) Appl. No.: 11/316,064

(22) Filed: Dec. 22, 2005

(65) Prior Publication Data
US 2006/0142829 A1 Jun. 29, 2006

(30) Foreign Application Priority Data
Dec. 23, 2004 (DE) .................. 10 2004 062 394

(51) Int. Cl.
*A61N 1/00* (2006.01)
(52) U.S. Cl. .................................... 607/120
(58) Field of Classification Search .......... 607/115–130
See application file for complete search history.

(56) References Cited

U.S. PATENT DOCUMENTS

| 4,922,926 A | | 5/1990 | Hirschberg et al. |
| 5,109,112 A | | 4/1992 | Siekierka et al. |
| 5,282,844 A | * | 2/1994 | Stokes et al. ................ 607/120 |
| 5,489,294 A | | 2/1996 | McVenes et al. |
| 5,496,360 A | * | 3/1996 | Hoffmann et al. ............ 607/120 |
| 5,522,874 A | * | 6/1996 | Gates .......................... 607/127 |
| 6,330,467 B1 | | 12/2001 | Creighton, IV et al. |
| 6,748,653 B2 | | 6/2004 | Lindemans et al. |
| 7,008,418 B2 | * | 3/2006 | Hall et al. ....................... 606/41 |
| 2002/0042645 A1 | | 4/2002 | Shannon |
| 2002/0123505 A1 | | 9/2002 | Mollison et al. |
| 2003/0100887 A1 | | 5/2003 | Scott et al. |
| 2003/0152609 A1 | | 8/2003 | Fischell et al. |
| 2004/0127886 A1 | * | 7/2004 | Daum ..................... 604/891.1 |
| 2004/0230274 A1 | | 11/2004 | Heil et al. |
| 2005/0058688 A1 | * | 3/2005 | Boerger et al. .............. 424/426 |
| 2005/0070985 A1 | * | 3/2005 | Knapp et al. ................ 607/122 |

FOREIGN PATENT DOCUMENTS

| EP | 0 030 953 B1 | 7/1981 |
| EP | 0 356 399 A2 | 2/1990 |
| EP | 0 534 401 B1 | 3/1993 |
| EP | 0 620 024 B1 | 10/1994 |
| EP | 0 701 802 B1 | 3/1996 |

\* cited by examiner

*Primary Examiner*—George Manuel
*Assistant Examiner*—Shubatra Narayanaswamy

(57) ABSTRACT

An intravenous pacemaker electrode has an electrode tip designed to release a drug, where the drug contains at least one of the active substances sirolimus, paclitaxel, everolimus, fibrin, rapamycin, and tacrolimus.

13 Claims, 5 Drawing Sheets

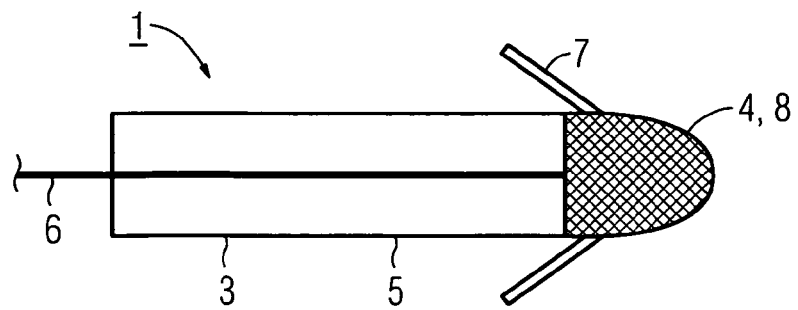
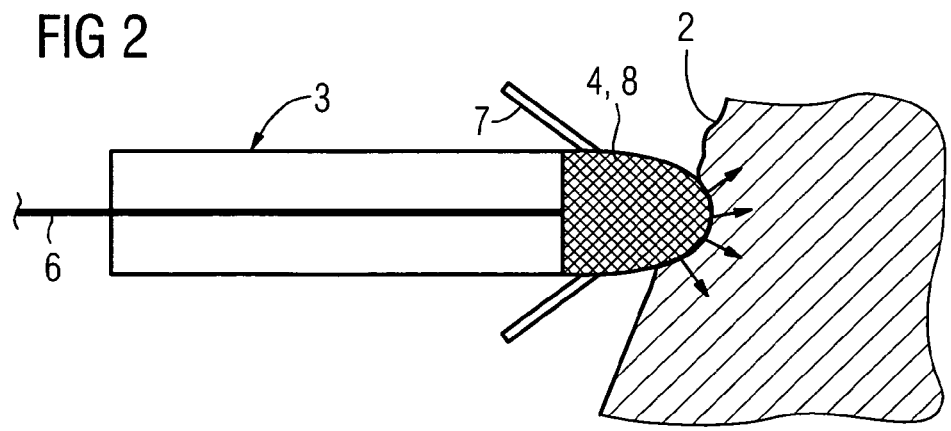

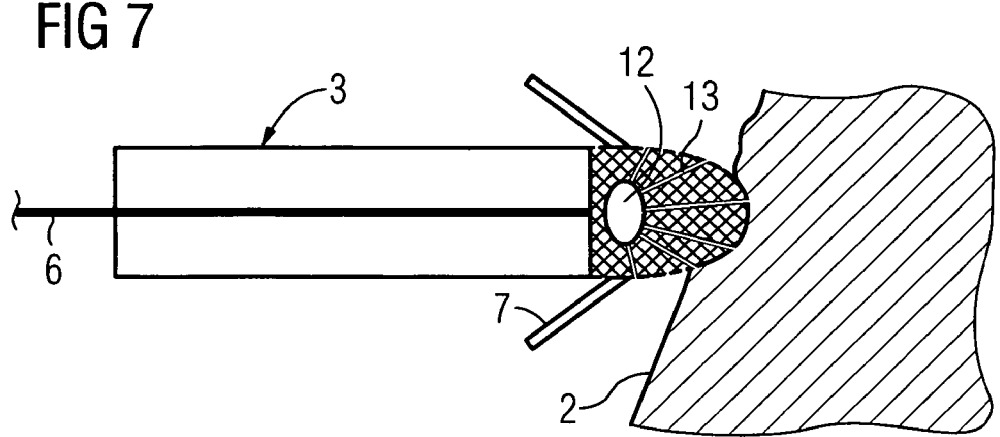
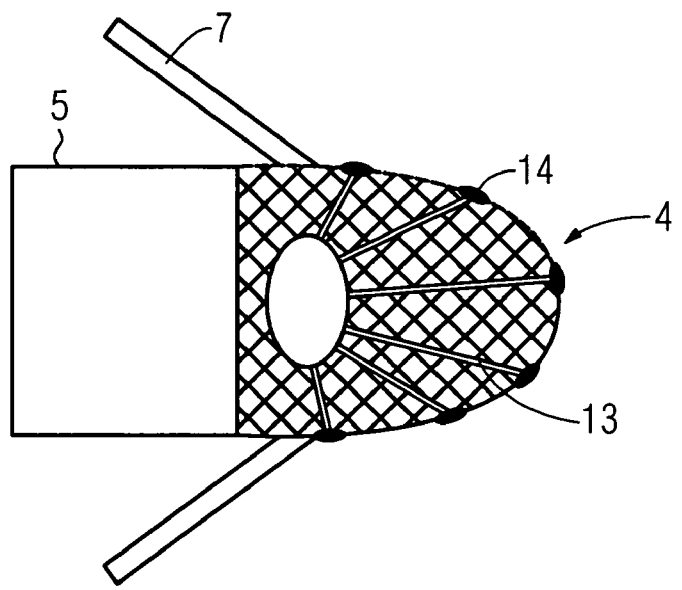

INTRAVENOUS PACEMAKER ELECTRODE

CROSS REFERENCE TO RELATED APPLICATION

This application claims priority of the German application No. 10 2004 062 394.5 DE filed Dec. 23, 2004, which is incorporated by reference herein in its entirety.

FIELD OF THE INVENTION

The invention relates to an intravenous pacemaker electrode that enables the release of a drug, and a method suitable for manufacturing such a pacemaker electrode.

BACKGROUND OF THE INVENTION

A pacemaker electrode intended for releasing a drug is known for example from U.S. Pat. No. 4,922,926.

Implantable pacemaker electrodes have an electrode tip, which must be fixed permanently to the myocardium. In addition to the mechanical anchoring of the electrode tip to the heart muscle, it should be ensured that electrical stimulation pulses can be transmitted under as constant conditions as possible. For this purpose, an electrode device for intracorporal stimulation of the body tissue, known from European patent EP 0 620 024 B1, for example has an electrode head whose surface layer is made of a conducting material, which is partially covered with a layer of high-resistance insulating material. The layer is designed to be so thin that the difference between the distance between the stimulation surface and the heart tissue and between the insulating layer and the heart tissue respectively for an applied electrode device does not result in a threshold effect.

The stimulation threshold of a pacemaker can change over time as a result of tissue fibrosis around the electrode tip. In the extreme case, such a change in the stimulation threshold results in the pacemaker no longer performing its intended function. In cases in which the pacemaker continues to perform its function despite an increase in the stimulation threshold, power consumption increases and hence the service life of the pacemaker battery decreases. For patients this means needing to have frequent checks by the doctor.

SUMMARY OF THE INVENTION

The object of the invention is to specify an implantable pacemaker electrode, which is distinguished by long-term usability combined with particularly low changes over time.

This object is achieved according to the invention by an implantable intravenous pacemaker electrode having the features of the claims, and by a method for manufacturing a pacemaker electrode having the features of the claims. The subclaims relate to advantageous embodiments and developments or independently inventive combinations of features. Advantages and developments cited below relating to the pacemaker electrode also apply analogously to the method and vice versa.

The pacemaker electrode has an electrode tip, preferably with a number of recesses, in which an active substance is held and/or on which an active substance is deposited. The amount of active substance and the release rate from the electrode tip are preferably designed so that the active substance is released from the implanted electrode tip continuously over a period of at least 1000 hours, preferably over a period of at least two months, for example about three months.

Tissue fibrosis can be prevented or at least curtailed by the long-lasting release of the active substance, so that the stimulation threshold of the pacemaker does not increase significantly. After the cited time periods of significantly more than one month, the immune system of the patient has typically become adjusted to the electrode tip to such an extent that no further tissue fibrosis occurs and hence the stimulation threshold of the pacemaker remains at least approximately constant. The invention can also be applied to other implantable medical products designed to deliver electrical pulses, in particular to ICDs (implantable cardioverters/defibrillators) and/or neurostimulators.

The drug released from the electrode tip contains at least one of the following active substances:

sirolimus, known for example from U.S. patent 2003/0100887 A1 and U.S. patent 2002/0042645 A1, paclitaxel, known for example from U.S. patent 2003/0100887 A1 and U.S. patent 2002/0042645 A1, everolimus, known for example from U.S. patent 2003/152609, fibrin, known for example from European patent EP 0 701 802 B1, rapamycin, known for example from U.S. patent 2002/0123505 A1, tacrolimus, known for example from European patent EP 0 356 399 A2 and U.S. Pat. No. 5,109,112, The first four active substances listed above (sirolimus, paclitaxel, everolimus and fibrin) are also used for stents (tubes inserted in vessels), which are suitable for releasing active substances. Sirolimus, also known as Rapamune, is an immunosuppressant that was developed to reduce organ rejection in the patient. Paclitaxel is classified as a natural product with an anti-tumor action and belongs to the group of antineoplastic agents. Everolimus is related to sirolimus and is also used to counter transplant rejection. Both substances are rapamycin analogs. The agent tacrolimus is also known as FK 506.

The agent fibrin, a naturally occurring polymer that is produced from fibrinogen during blood clotting under the action of thrombin, and is also used in fibrin glues during surgery, for example, has the additional advantage that it can help to increase the adhesion of the electrode tip to the myocardium.

The release rate of the active substance can be influenced, for example, by bioabsorbable materials, in particular polymers, or by biostable materials. In principle, measures described in connection with a drug-eluting stent (see list of active substances above and associated printed matter) are suitable here for influencing the activation and diffusion of the active substance. European patent EP 0 534 401 B1 describes a barrier layer made of an ion-exchange material that can be used for selective control of the release rate.

All the active substances cited can also be used in combinations. The drug eluted from the electrode tip can also contain the following substances alone or in combination:

actinomycin-d, methotrexate, doxorubicin, cyclophosphamide, 5-fluorouracil, 6-mercaptopurine, 6-thioguanine, cytoxan, cytarabinoside, cisplatin, chlorambucil, busulfan.

These active substances can be used in particular for preventing or suppressing unwanted cell growth. All the substances cited can also be combined with other pharmacological substances, in particular anti-inflammatory agents such as Aspirin or Ibuprofen. In general, a drug containing pharmacological, chemical, biological and/or genetic active substances can be released from the electrode tip. The active substances can form a thin layer on the electrode tip or be supplied continuously to the surface of the electrode tip from a reservoir located in the pacemaker electrode, as described in more detail below.

The electrode tip has an electrically conducting material, also referred to as the base material, which preferably contains platinum, carbon, titanium or combinations of these elements. The said elements are particularly suitable for implantable medical products because of their physiological properties.

A ceramic material, aluminum dioxide, polyurethane or a polymer is preferably provided as a coating material, which the active substance comes into contact with. In the latter case, coatings of meta-acrylate polymers are preferably used. The choice of coating material and the type of bond between the active substance and this material are jointly responsible for the release rate of the active substance from the electrode tip.

The electrical contact resistance of the electrode tip tends to be increased initially by the active substance. In order to reduce this effect, the active substance is preferably mixed with an electrolyte that reduces the electrical resistance. Over the service life of the pacemaker, the electrical contact resistance and hence the stimulation threshold is always significantly lower than in a pacemaker without drug release that has produced tissue fibrosis.

According to a preferred development, the electrode tip has different active substances at different positions, preferably set apart from each other. Equally, a mixture of active substances can also be applied or supplied to the electrode tip, where the composition of the mixture can be selected so that the individual active substances are mainly released in different time periods.

The active substance or active-substance combination is preferably introduced into the electrode tip in such a way that the release depends on the temperature, for example release occurs solely in the temperature range of 35° C. to 42° C. The temperature-dependent active-substance release can be realized in particular by a recess holding the active substance in the electrode tip being sealed by a material that can degrade as a function of the temperature, for example changes into the liquid phase within the temperature interval cited. Where there are different active substances at the electrode tip, these are preferably introduced into the electrode tip in such a way that they are released with a different distribution over time. In this way, the drug release can be continuously adjusted to the given medical requirements over the whole release period of more than one month. According to a development, the drug release takes place over a period of at least 10 years, for example about 15 years. This period is approximately equal to the service life of the pacemaker electrode. Even for such a long release of a drug from the pacemaker electrode, the first months after the implantation are the most significant.

Recesses in the electrode tip provided for holding the active substance or substances can have the widest range of shapes, even within one and the same electrode tip. According to a particularly simple embodiment, the recesses are formed as sealed wells on the surface of the electrode tip, where the wells can be arranged in a geometrically defined way on the surface of the electrode tip, or distributed irregularly, to form a rough surface overall. In the latter case, the surface roughness of the electrode tip has the function of providing better adhesion of the active substance, where the whole surface, which is at least very slightly roughened, can be covered with a thin active-substance layer. The rough surface of the electrode tip can be produced using etching techniques for example, even at the nanotechnology scale.

In the case of discrete defined wells on the surface of the electrode tip, the active substance lies preferably solely in the wells. This distribution of small volume of active substance concentrated approximately at points can be achieved by immersing the electrode tip initially in an immersion bath containing the active substance and thereby wetting it totally with active substance. After the active substance has dried on the surface of the electrode, it is abraded so that the active substance lying outside the wells is removed, and the underlying conductive surface of the electrode tip is re-exposed. The surface regions of the electrode tip outside the wells preferably occupy a larger total surface area than the wells. By this means, the electrode tip retains a low contact resistance, which, as mentioned above, can be further reduced by adding an electrolyte to the active substance. The thickness of the active-substance layer applied to the electrode tip can easily be controlled by the number of coating and subsequent drying processes. This also applies to cases in which the dried active-substance layer is not removed again from parts of the surface.

According to an alternative embodiment, the electrode tip is porous, at least in a section of it, the active substance being absorbed in the porous material. The recesses from which the active substance is released can in this case have structural sizes in the micron range. The porous volume area of the electrode tip is preferably connected to a reservoir inside the pacemaker electrode, from which, in particular by capillary forces, active substance is re-supplied to the surface of the electrode tip.

In a particularly advantageous embodiment, the electrode tip has through-openings out of which the active substance is released. The through-openings, unlike openings in a porous body, have a defined geometrical form and are preferably connected to an active-substance reservoir located inside the electrode tip or adjacent to the electrode tip. The openings formed as through-openings can be sealed at the surface of the electrode tip, as described above, with a material that unseals the opening as a function of the temperature.

Avoiding tissue fibrosis by means of continuous drug release from the electrode tip allows a particularly small design for the electrode tip. The surface area of the electrode tip is preferably less than 5 mm$^2$. Despite this small surface area, the stimulation threshold exhibits no time dependency or only very slight time dependency.

According to an advantageous development, the pacemaker electrode has a magnet at or near the electrode tip, in particular an electromagnet that enables navigation of the pacemaker electrode in the body using an external magnetic field. The principles of a system for magnetic navigation of a medical product in the body of a patient is known for example from U.S. Pat. No. 6,330,467 B1.

BRIEF DESCRIPTION OF THE DRAWINGS

An exemplary embodiment of the invention is described in more detail below with reference to a drawing, in which in the form of schematic diagrams:

FIG. 1,2 show a pacemaker electrode suitable for release of a drug,

DETAILED DESCRIPTION OF THE INVENTION

Figure 3:
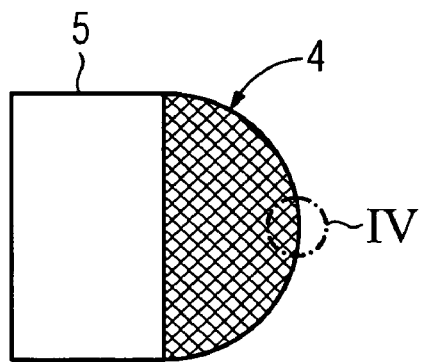
FIG. 3,4 show sections of the pacemaker electrode according to FIG. 1,2.

Corresponding parts, or parts with the same function, are given the same references in all figures.

FIGS. 1 and 2 show schematically part of a pacemaker electrode 1 for transmitting stimulation pulses to a myocardium 2. The pacemaker electrode may be from a unipolar pacemaker or equally from a bipolar pacemaker, where in each case it is possible not only to transmit stimulation pulses to the myocardium, but also to detect, or sense, signals coming from the heart. An electrode tip 4 is attached to the distal end of an electrode cable 3 of the pacemaker electrode 1. An electrical conductor 6 runs inside the electrode cable 3, which has an insulating sleeve 5, up to the electrode tip 4. Two fold-out anchoring flaps 7 are attached to this tip, which act like an expandable anchor to enable or facilitate the anchoring of the electrode tip 4 in the tissue of the patient. The anchoring aids 7 may also differ from the simplified diagram, for example they may have a form known from the German patent DE 33 00 050 C2.

Figure 4:
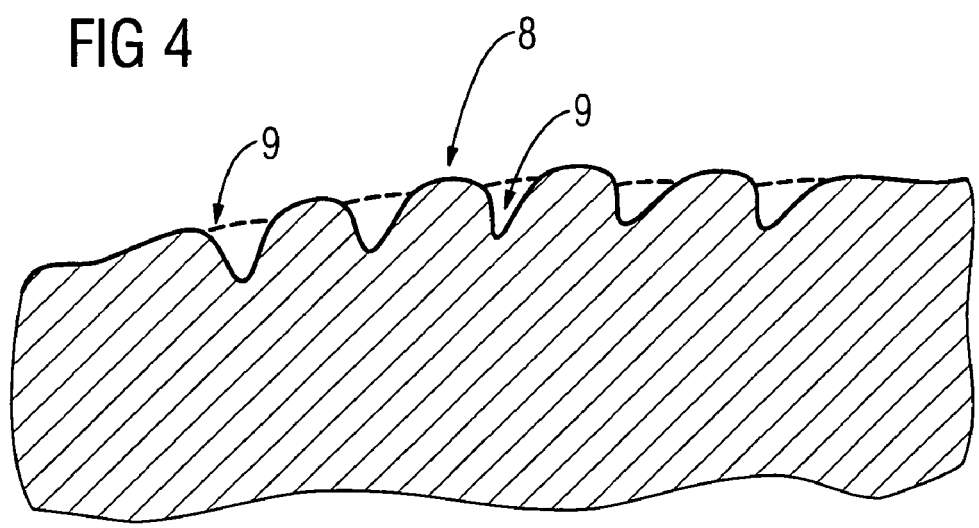
Figure 5:
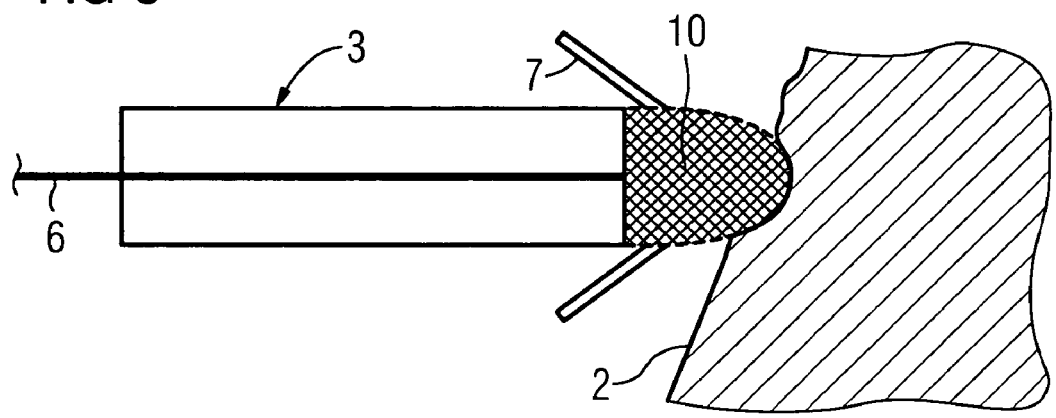
FIG. 5 shows a pacemaker electrode with an electrode tip having a lattice structure.

The design of the surface of the electrode tip 4 can be seen in more detail in FIGS. 3 and 4. The surface labeled 8 of the electrode tip 4 is roughened to form discrete recesses 9. In FIG. 1 to 3, these recesses are represented by a regular pattern, but may actually be randomly distributed on the surface 8, even in microscopic form. A supply of a drug that contains, or is, one of the active substances sirolimus, paclitaxel, everolimus, fibrin, rapamycin and/or FK 506 is held in each recess 9. Furthermore, the electrode tip 4 is made of a conducting material such as carbon, titanium or platinum, which is provided, in a way not shown, with a coating, preferably made of a ceramic material, aluminum dioxide, a polymer or polyurethane, which acts as a substrate material for said drug. The electrode tip can also have a coating of iridium, for example, which is covered directly or indirectly with active substance. If necessary, an active substance can be applied not only to the electrode tip 4 but also to the insulating sleeve 5, in the form of a layer or in any other form.

The active substance deposited in the recesses 9 for preventing tissue fibrosis at the contact point between the electrode tip 4 and the heart tissue is mixed both with an electrolyte that increases the conductivity and with a substance that increases the surface adhesion. Together with the geometrical design of the recesses 9 and the given chemical conditions in the body, this results in a drug release period in the implanted state of the pacemaker electrode 1, as shown in FIG. 2, of about three months. Tissue fibrosis in the area where the myocardium 2 makes contact with the pacemaker electrode 1 is thereby permanently avoided.

Various alternative embodiments of pacemaker electrodes 1 are shown in FIG. 5 to 10. In the exemplary embodiment according to FIG. 5, the electrode tip 4 has a regular lattice structure 10, which performs the same function as the rough surface 8 in the exemplary embodiment shown in FIG. 1 to 4.

Figure 6:
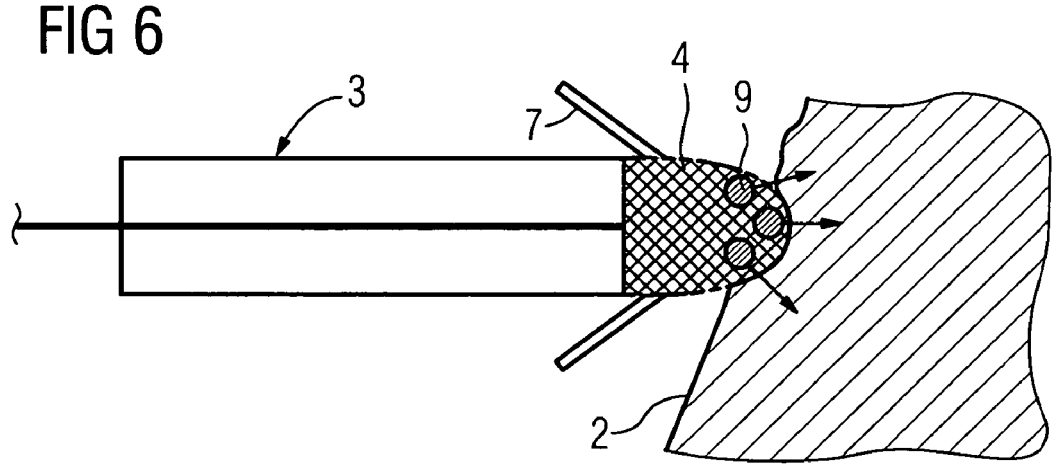
FIG. 6 shows a pacemaker electrode with an electrode tip having different active substances, FIG. 7,8 show a pacemaker electrode with an electrode tip having capillary tubes and a reservoir for an active substance.

In the exemplary embodiment according to FIG. 6, the electrode tip 4 has three different active substances that can defuse into the myocardium 2. In this case, the release conditions of the different active substances are set so that the active substances are mainly released consecutively in time, where the individual release periods can lie between a few minutes and several months.

Whereas in the exemplary embodiments according to FIG. 1 to 6 the active substance or substances are deposited solely on the surface of the electrode tip 4, in the exemplary embodiments according to FIG. 7 to 10, the inside of the electrode tip 4 is also used for storing and/or conveying a drug. In the exemplary embodiment according to FIGS. 7 and 8, a reservoir 12 filled with the drug to be released is located inside the electrode tip 4. Capillary tubes 13 run from the reservoir 12 to the surface of the electrode tip 4. In order to enable a controlled release of the drug from the electrode tip 4, the recesses 9 on the surface of the electrode tip 4, which double as the openings of the capillary tubes 13, are initially sealed with a sealing material 14. The properties of the sealing material 14 are selected so that the openings 9 of the electrode tip 4 lying next to the myocardium 2 are unsealed at a temperature of 35° C. to 42° C.

Figure 9:
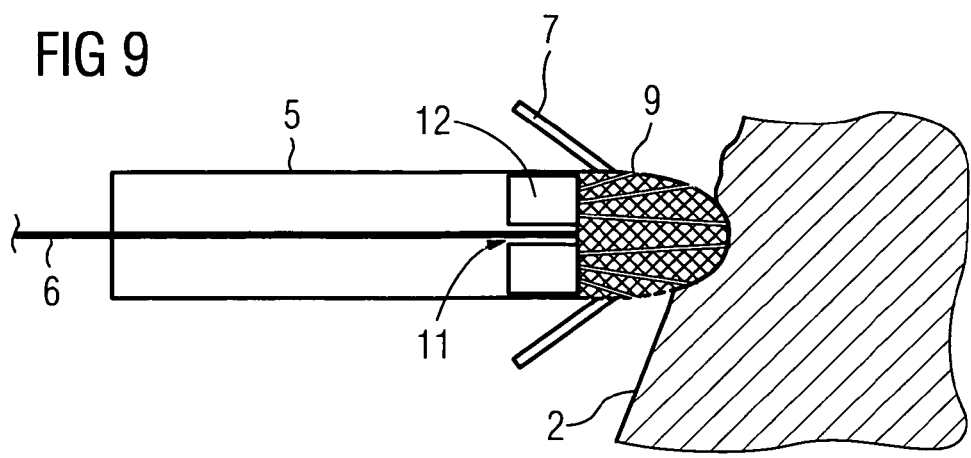
FIG. 9 shows a pacemaker electrode with an electrode tip having capillary tubes, and an active-substance reservoir located beside said electrode tip.

The exemplary embodiment according to FIG. 9 essentially differs from the exemplary embodiment according to FIGS. 7 and 8 in that the reservoir 12 is not arranged inside the electrode tip 4 but is adjacent to this. The reservoir 12 is annular in shape in this case, having a central through-opening 11, and the conductor 6 leading to the electrode tip 4 runs through it.

Figure 10:
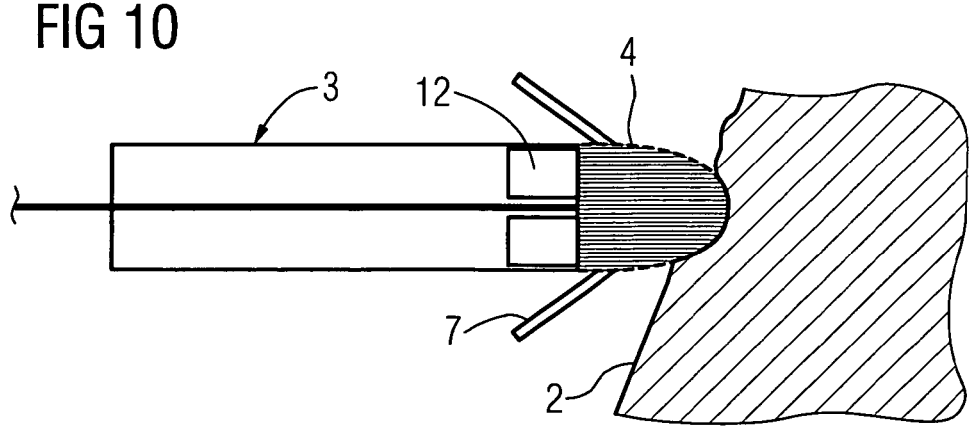
FIG. 10 shows a pacemaker electrode with a porous electrode tip and a reservoir for an active substance.

In the exemplary embodiment according to FIG. 10, the electrode tip 4 has no capillary tubes of defined geometrical design, but is porous overall in order to achieve a comparable effect. In this case the active substance stored in the reservoir 12 is again continuously released by the electrode tip 4 to the myocardium 2.

The invention claimed is:

1. An intravenous pacemaker electrode comprising an electrode tip adapted for releasing a drug,
    wherein the drug is selected from the group of active substances consisting of: sirolimus, fibrin, rapamycin, tacrolimus, and combinations thereof
    wherein a plurality of recesses in the electrode tip hold the drug,
    wherein the active substances are introduced into the electrode tip such that the release depends on the temperature, and
    wherein the plurality of recesses in the electrode tip that hold the drug are sealed by a material that degrades as a function of the temperature.

2. The pacemaker electrode according to claim 1, wherein the amount of active substance and the release rate from the electrode tip are designed so that the active substance is released from the implanted electrode tip over a period of at least 1000 hours.

3. The pacemaker electrode according to claim 2, wherein the active substance is released from the implanted electrode tip over a period of at least 10 years.

4. The pacemaker electrode according to claim 1, wherein the electrode tip comprises a coating material selected from the group consisting of: platinum, carbon, titanium, aluminum dioxide, polyurethane, and a polymer.

5. The pacemaker electrode according to claim 4, wherein the polymer is a methacrylate polymer.

6. The pacemaker electrode according to claim 1, wherein the active substance is mixed with an electrolyte to increase the conductivity.

7. The pacemaker electrode according to claim 1, wherein the electrode tip has different active substances at different positions on the electrode tip.

8. The pacemaker electrode according to claim 1, wherein different active substances are introduced into the electrode tip such that they are released with a different distribution over a time interval.

9. The pacemaker electrode according to claim 1, wherein the active substance is held in a porous structure of the electrode tip.

10. The pacemaker electrode according to claim 1, wherein the plurality of recesses holding the active substance in the electrode tip are through-openings.

11. The pacemaker electrode according to claim 10, wherein the through-openings are connected to an active-substance reservoir.

12. The pacemaker electrode according to claim 1, wherein the electrode tip has a surface area of less than 5 square millimeters.

13. The pacemaker electrode according to claim 1, wherein the electrode tip is navigated by a magnetic field.

* * * * *

UNITED STATES PATENT AND TRADEMARK OFFICE
CERTIFICATE OF CORRECTION

PATENT NO. : 7,643,885 B2  Page 1 of 1
APPLICATION NO. : 11/316064
DATED : January 5, 2010
INVENTOR(S) : Michael Maschke It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1021 days.

Signed and Sealed this

Sixteenth Day of November, 2010

David J. Kappos
*Director of the United States Patent and Trademark Office*